(12) United States Patent
Xie et al.

(10) Patent No.: US 11,179,409 B2
(45) Date of Patent: Nov. 23, 2021

(54) CUCURBITANE TETRACYCLIC TRITERPENOID COMPOUNDS FOR APPLICATION IN TREATING PULMONARY FIBROSIS

(71) Applicant: CHENGDU BIOPURIFY LTD., Chengdu (CN)

(72) Inventors: Haifeng Xie, Chengdu (CN); Chaofeng Zhang, Chengdu (CN); Qilin Xie, Chengdu (CN); Yunling Hu, Chengdu (CN)

(*) Notice: Subject to any disclaimer, the term of this patent is extended or adjusted under 35 U.S.C. 154(b) by 0 days.

(21) Appl. No.: 16/022,654

(22) Filed: Jun. 28, 2018

(65) Prior Publication Data
US 2018/0303860 A1 Oct. 25, 2018

Related U.S. Application Data

(63) Continuation of application No. PCT/CN2016/086863, filed on Jun. 23, 2016.

(30) Foreign Application Priority Data

Dec. 29, 2015 (CN) .......................... 201511008841.8

(51) Int. Cl.
A61K 31/704 (2006.01)
A61K 31/575 (2006.01)
A61P 11/00 (2006.01)

(52) U.S. Cl.
CPC .......... *A61K 31/704* (2013.01); *A61K 31/575* (2013.01); *A61P 11/00* (2018.01)

(58) Field of Classification Search
CPC ... A61K 31/704; A61K 31/575; A61K 31/191
See application file for complete search history.

(56) References Cited

U.S. PATENT DOCUMENTS

2014/0308698 A1* 10/2014 Liu .......................... C12P 19/18
435/53

OTHER PUBLICATIONS

Medbroad cast, 2017.*
Internation Search Report of PCT/CN2016/086863, dated Sep. 14, 2016.
Shi, Dongfang et al."Protective effects and mechanisms of mogroside V on LPS-induced acute lung injury in mice" Pharmaceutical Biology, vol. 52, No. 6, Jun. 30, 2014 (Jun. 30, 2014), ISSN: 1388-0209.

* cited by examiner

*Primary Examiner* — Pancham Bakshi

(57) ABSTRACT

An application of cucurbitane tetracyclic triterpenoid compounds in preparation of drugs and/or health products for preventing and/or treating pulmonary fibrosis is provided, which is a new medicine use of cucurbitane tetracyclic triterpenoid compounds.

3 Claims, 7 Drawing Sheets

CUCURBITANE TETRACYCLIC TRITERPENOID COMPOUNDS FOR APPLICATION IN TREATING PULMONARY FIBROSIS

CROSS-REFERENCE TO RELATED APPLICATIONS

This application is a continuation of International Patent Application No. PCT/CN2016/086863 with a filing date of Jun. 23, 2016, designating the United States, now pending, and further claims priority to Chinese Patent Application No. 20151100884 1. 8 with a filing date of Dec. 29, 2015. The content of the aforementioned applications, including any intervening amendments thereto, are incorporated herein by reference.

TECHNICAL FIELD

The disclosure belongs to the technical field of prevention and treatment of pulmonary fibrosis, and relates to an application of cucurbitane tetracyclic triterpenoid compounds in preparation of drugs and/or health products for preventing and/or treating pulmonary fibrosis.

BACKGROUND OF THE PRESENT INVENTION

Pulmonary fibrosis (PF) is a chronic interstitial lung disease characterized by infiltration of inflammatory cells such as lymphocytes and macrophages in lung mesenchyme, proliferation of fibroblasts, and deposition of fibrous connective tissues in lung mesenchyme. Pulmonary fibrosis is caused by a variety of pathogenic factors both inside and outside lungs, is a consequence that a series of chronic lung injuries or diseases are developed to be in a late stage, and seriously threatens human health. The causes of pulmonary fibrosis include hereditary immunologic dysfunction, virus infection, drugs and chemicals, radioactive rays, air pollution (haze, smoke, dust) and other factors. With a complex pathophysiological process, pulmonary fibrosis is dominated by pulmonary inflammation with significant inflammatory cellular infiltration and diffuse thickened pulmonary alveolar wall in an early stage. In the middle and advanced stage, a large amount of collagen fibers are generated and deposited, with alveolar deformation and atresia, and the normal lung tissue structure is damaged with loss of functions. The main clinical manifestations of pulmonary fibrosis include stimulating dry cough, restrictive ventilatory dysfunction, progressive dyspnea, reduction of diffusion function, hypoxemia and the like. In recent years, due to increase of incidence year by year, pulmonary fibrosis is still a disease with high mortality rate, and lacks effective treatment means in clinic. The traditional therapeutic drugs are still mainly anti-inflammatory, immunosuppressive and anticoagulant, and glucocorticoid, cyclophosphamide, cyclosporine, colchicine and penicillamine are clinically used but have poor efficacy and large side effects. Therefore, it is an urgent need for the current medicine that effective pulmonary fibrosis-resisting drugs are found.

Related studies have shown that in a body, many cytokines can influence formation and development of pulmonary fibrosis, such as a transforming growth factor-$\beta 1$ (TGF-$\beta 1$), a connective tissue growth factor (CTGF) and a platelet derived growth factor (PDGF) that can promote formation of fibrosis, and a tumor necrosis factor-$\alpha$ (TNF-$\alpha$), interleukin-6 (IL-6) and interleukin-17 (IL-17) that participate in local injury and inflammatory reaction. The interaction between these cytokines and interaction between these cytokines and inflammatory cells as well as lung tissue cells aggravate inflammation or immune injury of lung tissues, stimulate proliferation and differentiation of fibroblasts, promote generation and deposition of an extracellular matrix and play an important role in the process of pulmonary fibrosis. TGF-$\beta 1$ plays an important role, is capable of promoting phenotypic transformation of myofibroblasts, stimulating synthesis and secretion of a plurality of cytokines and regulating proliferation and differentiation of cells and the like, is a potent fibrosing factor, can stimulate synthesis of cells and secrete the extracellular matrix (ECM), and can also change activities of degrading enzyme components of the matrix to directly aggravate the deposition of ECM. In the pathogenesis of pulmonary fibrosis, activation and proliferation of myofibroblasts play a key role and a large amount of pro-fibrogenic factors are released at the same time, so as to increase expression of smooth muscle actin $\alpha$-SMA and accumulation of collagens, thereby resulting in the deposition of ECM and eventually causing pulmonary fibrosis. The development of drugs for treating pulmonary fibrosis with inhibition of pro-fibrogenic factors as a starting point is a research hotspot at present.

Lung lipid peroxidation injury is also called ventilator-induced lung injury, and meanwhile is possibly one of mechanisms that macrophages are activated and cytokines are released so as to promote formation of pulmonary fibrosis. Malondialdehyde (MDA) is one of main products generated by peroxidation of lipid in a body. The level of MDA can indirectly reflect the ability of the body to eliminate oxygen free radicals and the severity degree of cells attacked by free radicals. In case of over-high concentration of nitric oxide (NO), excessive toxic intermediates are generated to aggravate injury of cells; generation of a huge amount of NO in the lung tissue has an effect of aggravating the lung injury and promoting the proliferation of myofibroblasts. The metabolic disorder of these oxidation-related indexes in the body promotes the occurrence and progress of pulmonary fibrosis, and regulation of balance of these indexes is beneficial to treatment of pulmonary fibrosis.

The animal model for bleomycin-induced mice pulmonary fibrosis through tracheal administration is a classic animal model for study on drugs for pulmonary fibrosis at home and abroad. The pulmonary fibrosis animal model replicated by this method is similar to a human pulmonary fibrosis model, and can induce generation of tissue inflammation and fibrosis in a short time to cause imbalance of oxidation and antioxidation in the body, and increase the expression of pro-inflammatory factor IL-6 and pro-fibrotic markers TGF-$\beta 1$ and $\alpha$-SMA and the like, thereby leading extracellular matrix deposition and fibrous tissue proliferation to form pulmonary fibrosis.

At present, drugs for treating pulmonary fibrosis are mainly glucocorticoid, cytotoxic drugs, immunosuppressants, and immunomodulators. However, no specific drugs are available. Therefore, it is necessary to develop a novel efficient and safe drug for treating pulmonary fibrosis.

So far, there are no reports about the application of cucurbitane tetracyclic triterpenoid compounds in treating pulmonary fibrosis.

SUMMARY OF PRESENT INVENTION

The disclosure discloses a new use of cucurbitane tetracyclic triterpenoid compounds in preparation of drugs and/or health products for preventing and/or treating pulmonary fibrosis.

The technical solutions of the disclosure are as follows:

The disclosure discloses an application of cucurbitane tetracyclic triterpenoid compounds in preparation of drugs and/or health products for preventing and/or treating pulmonary fibrosis.

The structural formula of the cucurbitane tetracyclic triterpenoid compounds is as shown in a formula I:

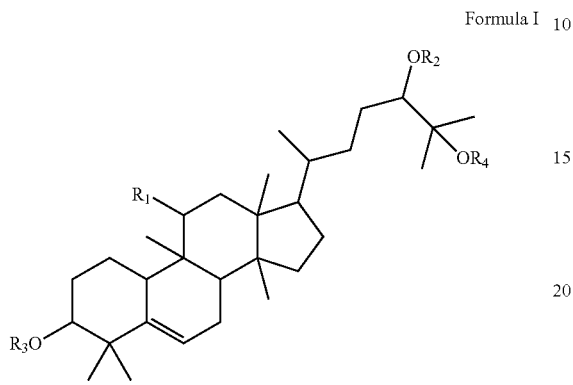

Formula I wherein, R1 is hydroxyl or carbonyl; R2, R3 and R4 are hydrogen or glycosyl; glycosyl is hexapyranose, pentapyranose, hexafuranose, pentafuranose, or diglycosyl, triglycosyl and tetraglycosyl formed therefrom.

Preferably, in the formula I, R1 is hydroxyl.

Preferably, in the formula I, R4 is hydrogen.

Preferably, in the formula I, R2 is hydrogen, R3 is hydrogen or glycosyl; more preferably, the glycosyl is hexapyranose, or diglycosyl, triglycosyl and tetraglycosyl formed therefrom; more preferably, the glycosyl is diglycosyl or triglycosyl of hexapyranose.

Furthermore, the structural formula of the cucurbitane tetracyclic triterpenoid compounds is as follows: mogroside IIIe (formula II), mogroside III A1 (formula III), mogroside IVe (formula IV), mogroside V (formula V), mogroside II A2 (formula VI), mogroside I E1 (formula VII), 11-oxo-mogroside V (formula VIII) or mogrol (formula IX):

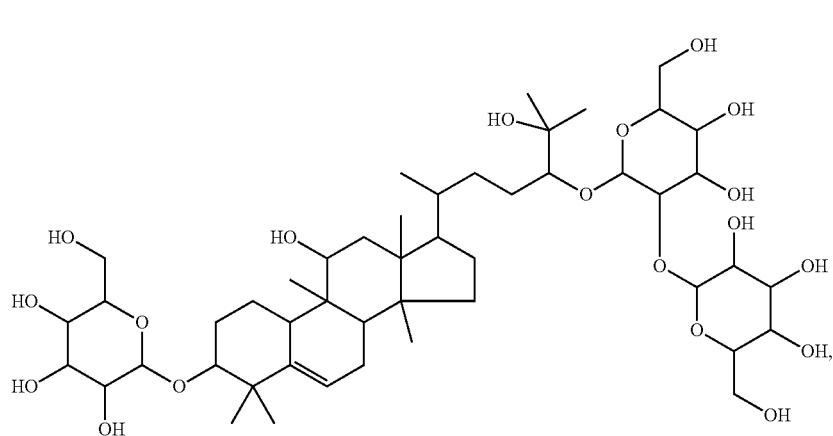

Formula II

Formula III
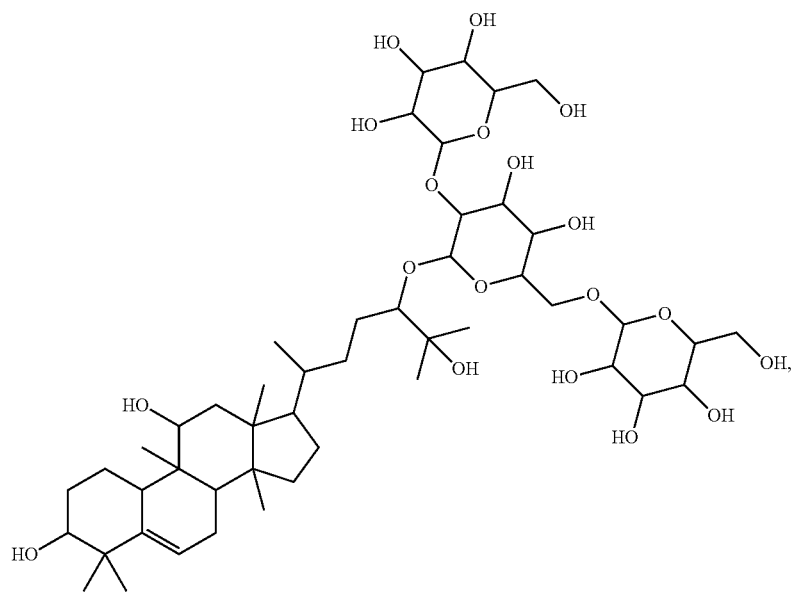
Formula IV
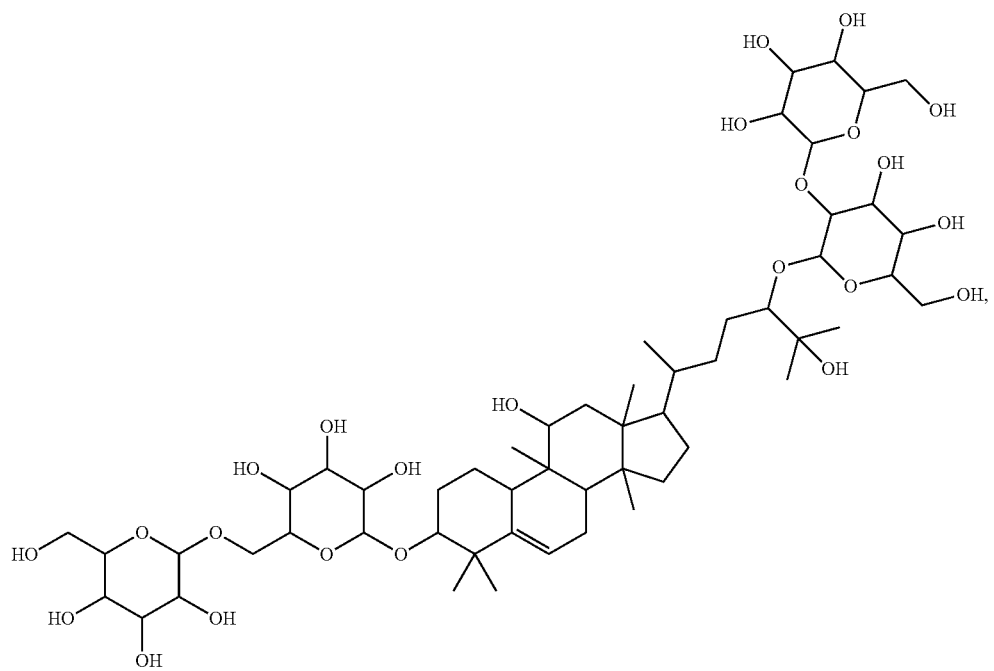

-continued
Formula V
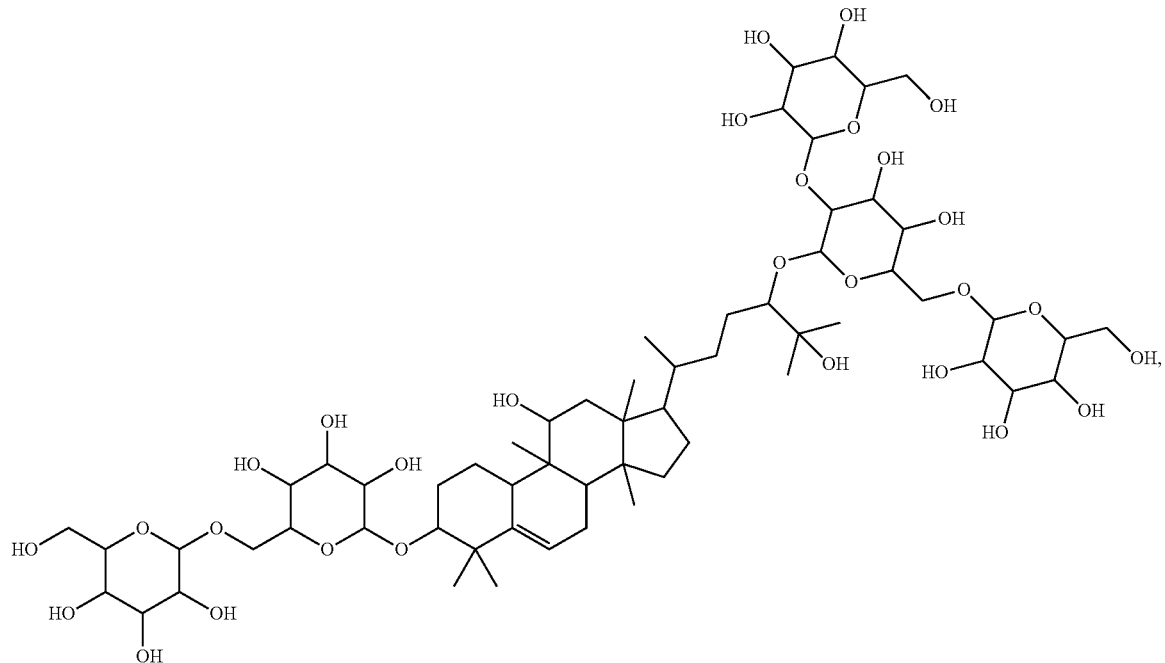
Formula VI
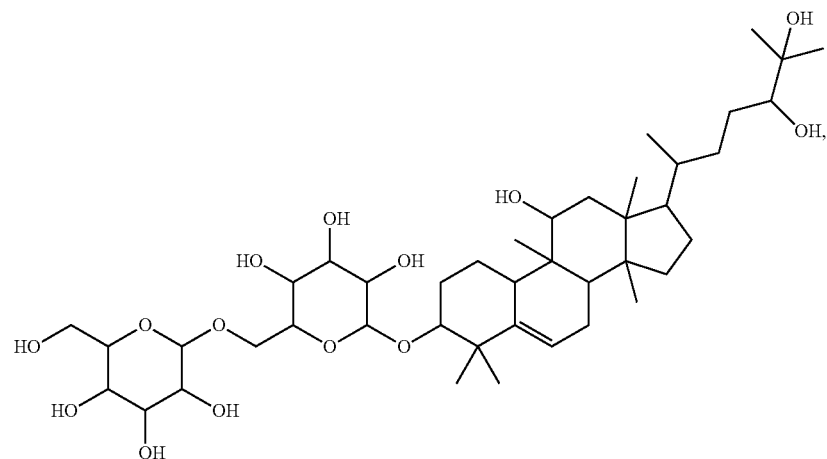
Formula VII
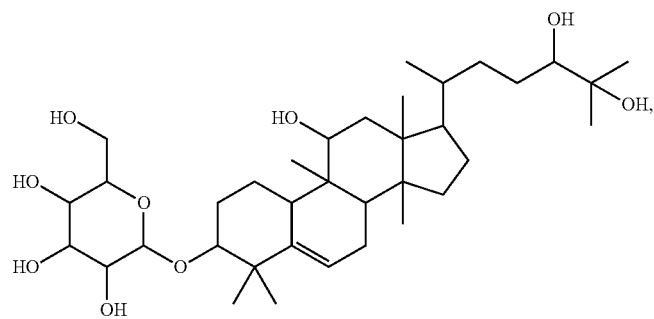

-continued
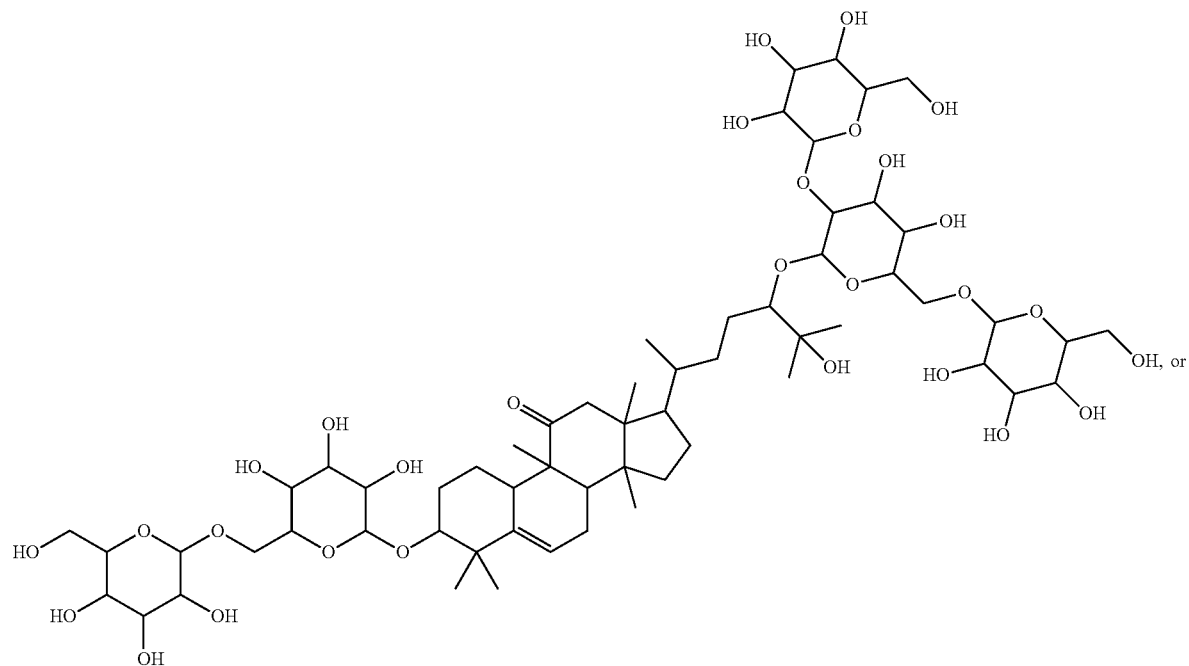
Formula VIII
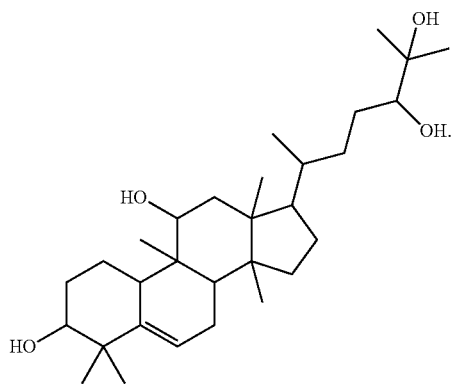
Formula IX

More preferably, the structural formula of the cucurbitane tetracyclic triterpenoid compound is formula II, formula IV or formula IX.

In the application of the aforementioned cucurbitane tetracyclic triterpenoid compounds in preparation of drugs and/or health products for preventing and/or treating pulmonary fibrosis, a compound as shown in formula I and a combination thereof as well as other human-acceptable pharmaceutical adjuvants are prepared into tablets, granules, decoctions or capsules.

The cucurbitane tetracyclic triterpenoid compounds are drugs and/or health products capable of reducing the accumulation volume of collagens in pulmonary fibrosis mesenchyme.

The cucurbitane tetracyclic triterpenoid compounds are drugs and/or health products capable of relieving inflammation, inhibiting collagen formation and protecting lung tissue against pulmonary fibrosis.

The cucurbitane tetracyclic triterpenoid compounds are drugs and/or health products capable of resisting pulmonary fibrosis by resisting inflammation and inhibiting alveolar epithelial-mesenchymal transition.

Beneficial Effects

1. Pulmonary fibrosis is a common pathological change generated when multiple lung diseases or lung injuries are developed into be in a late stage. A clinical study result shows that the survival rate of patients after pulmonary fibrosis is treated with glucocorticoid has no significant change, and no clear therapeutic drugs are available at present. The cucurbitane tetracyclic triterpenoid compounds of the disclosure are prepared from the traditional Chinese medicine *Momordica grosvenori* capable of moistening lung for arresting cough. At present, there are no any studies to report that mogroside components can be used for treatment of pulmonary fibrosis. The inventors have demonstrated that mogroside IIIe, mogroside IVe and aglycone-mogrol of mogroside components can significantly improve bleomycin-induced mice pulmonary fibrosis via in-vivo experiments. Mogroside IIIe, mogroside IVe and mogrol of the disclosure have good stability and can be used for preparing drugs for treating corresponding diseases.

2. Specifically, the experimental results of the disclosure show that, in the mogroside IIIe administration group of Example 1, Masson staining pathological sections show that the degree of pulmonary fibrosis in the administration groups is obviously improved, and the number of leukocytes in the bronchoalveolar fluid of the mogroside IIIe administration group is significantly lower than that in the model group. On the 28 d after administration, the content of TNF-α in the lung tissue and contents of HYP and TGF-β1 reflecting collagen deposition are significantly lower than those in the model group ($P<0.05$ or $P<0.01$). It indicates that mogroside IIIe has a certain therapeutic effect on pulmonary fibrosis at different stages, and the in-vivo experiment proves that mogroside IIIe has the effects of relieving the degree of inflammation and inhibiting the formation of collagen to protect the lung tissue.

The in-vitro experiment indicates that mogroside IIIe has an anti-inflammatory effect. Within a range of 10-100 μM, mogroside IIIe is of dose dependence to inhibit the level of NO in LPS-induced RAW264.7 cells. This result also confirms that mogroside IIIe has the effect of inhibiting epithelial-mesenchymal transition of TGF-β1-inducted Type II alveolar epithelial cells A549, and discloses that mogroside IIIe can take a medicine use of resisting pulmonary fibrosis by resisting inflammation and inhibiting alveolar epithelial-mesenchymal transition. Therefore, it illustrates that mogroside IIIe has a certain therapeutic effect on pulmonary fibrosis of model mice.

3. The experimental materials involved in the disclosure are derived from original plants. The original plants have wide range, low cost, clear extract activity and wide practical value.

DETAILED DESCRIPTION OF PREFERRED EMBODIMENTS

Figure 1:
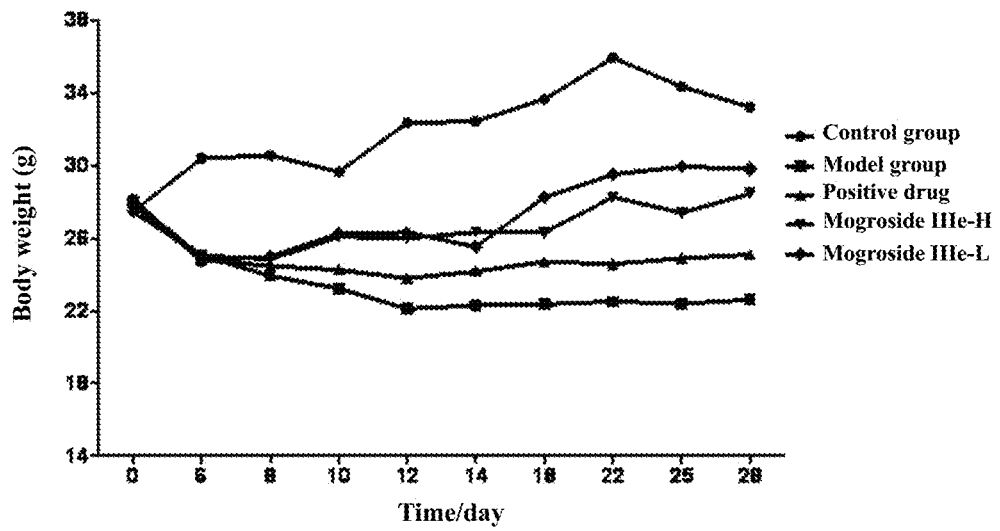
FIG. 1 is a schematic diagram showing change trend of mogroside IIIe on body weights of bleomycin-induced pulmonary fibrosis model mice; compared with the control group, #$p<0.05$; compared with the model group, *$p<0.05$, **$p<0.01$; positive control drug: prednisone acetate.

The disclosure discloses an application of the cucurbitane tetracyclic triterpenoid compound as shown in formula I in preparation of drugs and/or health products for preventing and/or treating pulmonary fibrosis. In the formula I, R1 is hydroxyl or carbonyl; R2, R3 and R4 are hydrogen or glycosyl; glycosyl is hexapyranose, pentapyranose, hexafuranose, pentafuranose, or diglycosyl, triglycosyl and tetraglycosyl formed therefrom.

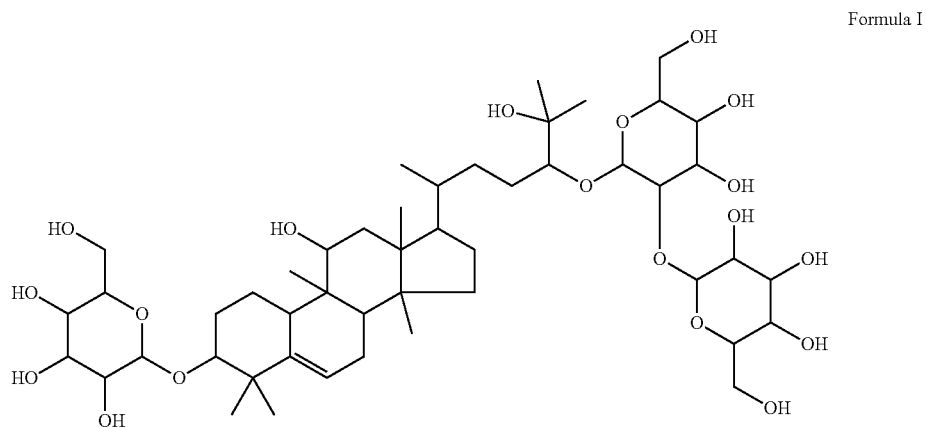 [SMILES: CC(CCC(OC1OC(CO)C(O)C(O)C1OC1OC(CO)C(O)C(O)C1O)C(C)(C)O)C1CCC2(C)C3CC=C4C(CCC(OC5OC(CO)C(O)C(O)C5O)C4(C)C)C3(C)C(O)CC12C]

Formula I

Preferably, in the formula I, R1 is hydroxyl.
Preferably, in the formula I, R4 is hydrogen.
Preferably, in the formula I, R2 is hydrogen, R3 is hydrogen or glycosyl; more preferably, the glycosyl is hexapyranose or diglycosyl, triglycosyl or tetraglycosyl formed therefrom; more preferably, the glycosyl is diglycosyl or triglycosyl of hexapyranose.
Preferably, in the formula I, R2 is glycosyl, R3 is hydrogen or glycosyl; more preferably, the glycosyl is hexapyranose or diglycosyl, triglycosyl or tetraglycosyl formed therefrom; more preferably, the glycosyl is diglycosyl or triglycosyl of hexapyranose.

Furthermore, the mogroside compounds are selected from one of the following compounds: mogroside IIIe (formula II), mogroside III A1 (formula III), mogroside IVe (formula IV), mogroside V (formula V), mogroside II A2 (formula VI), mogroside I E1 (formula VII), 11-oxo-mogroside V (formula VIII) or mogrol (formula IX):

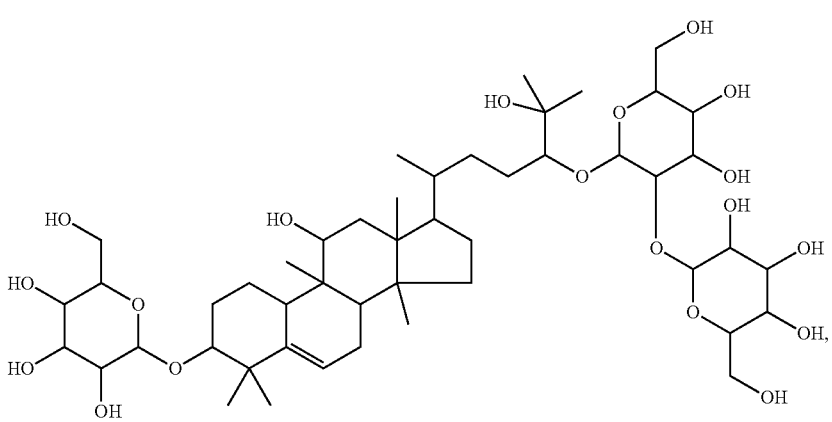

Formula II

Formula III
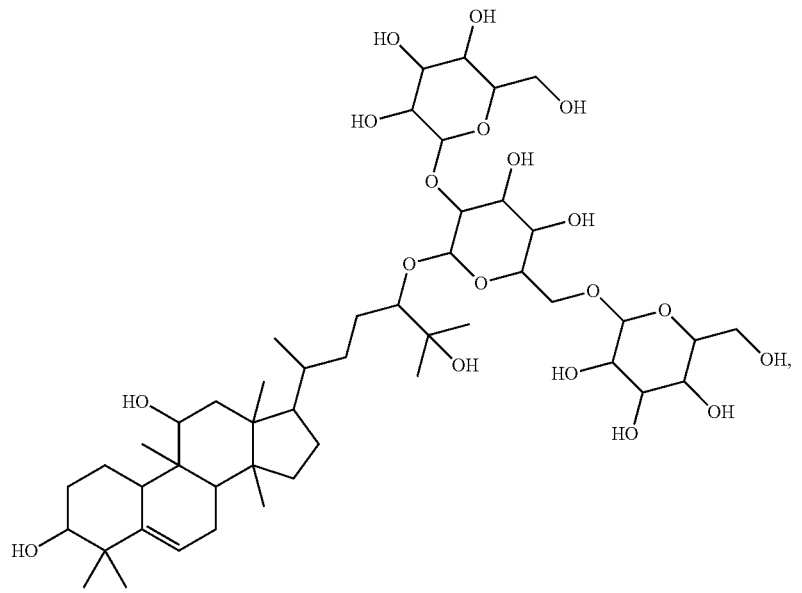
Formula IV
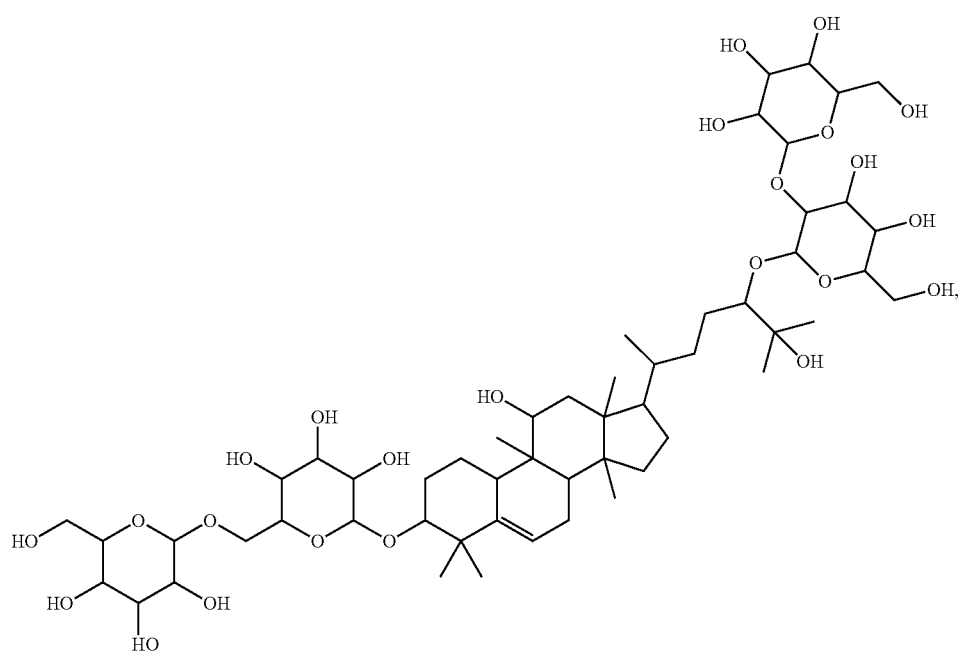

-continued
Formula V
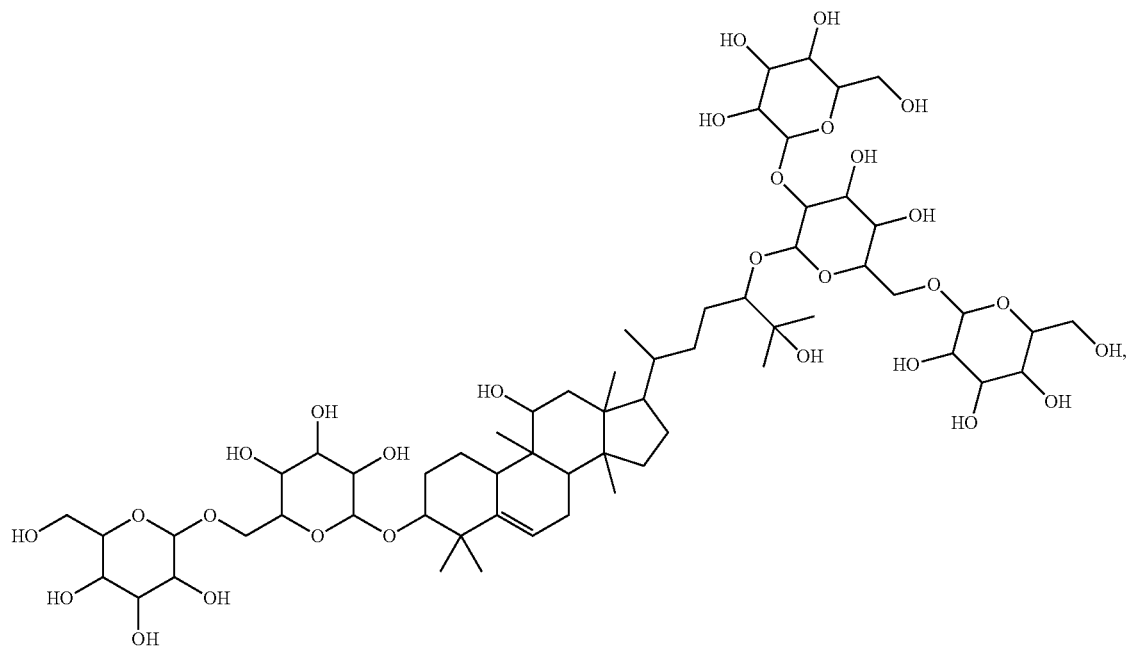
Formula VI
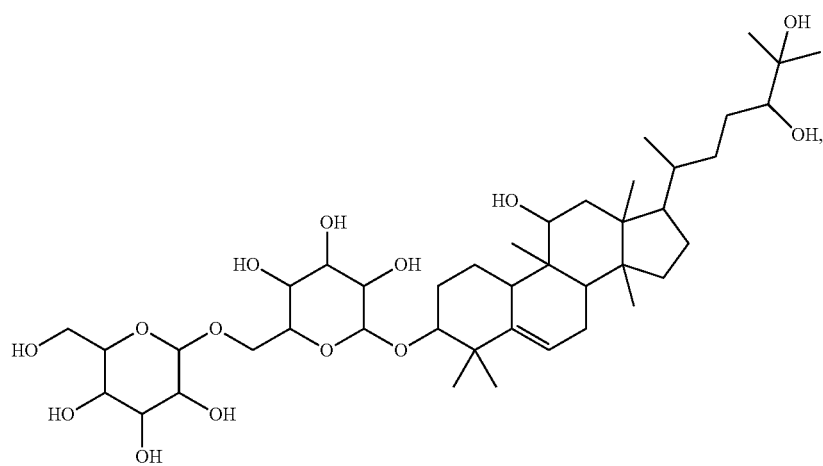
Formula VII
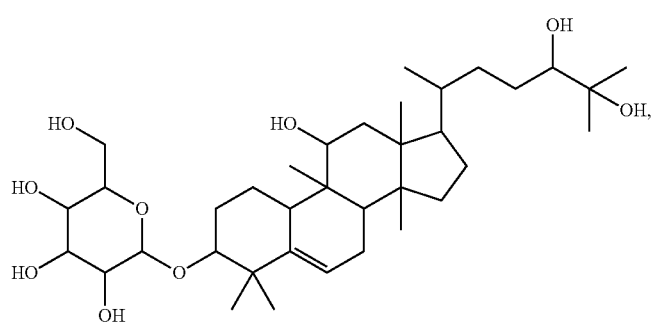

-continued

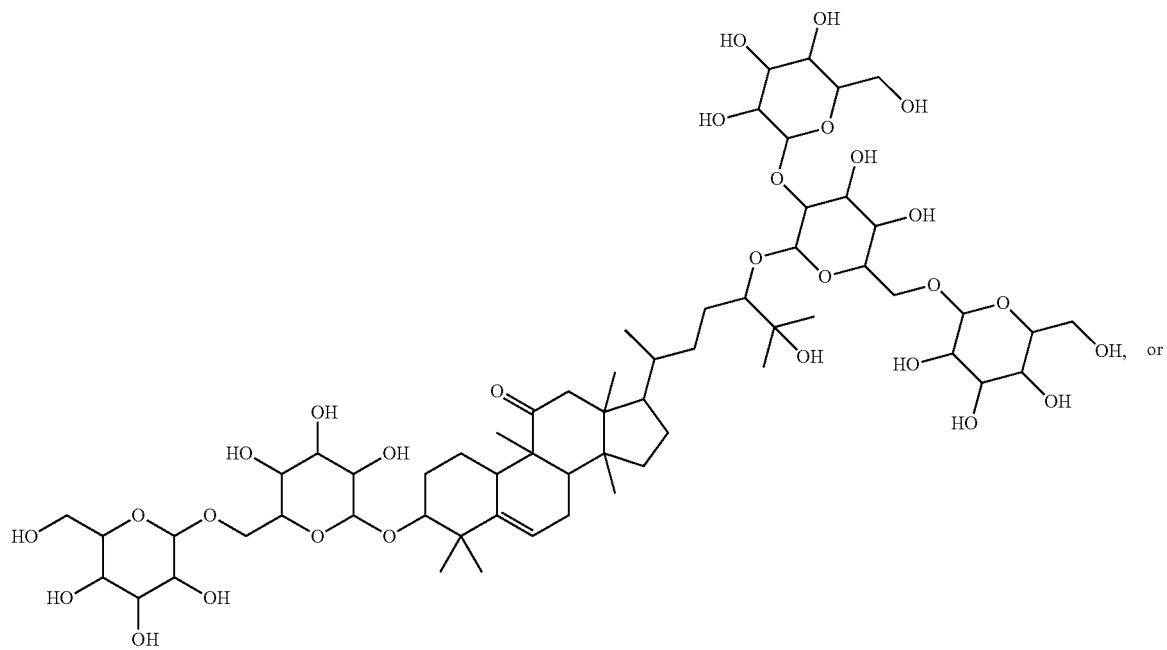

Formula VIII

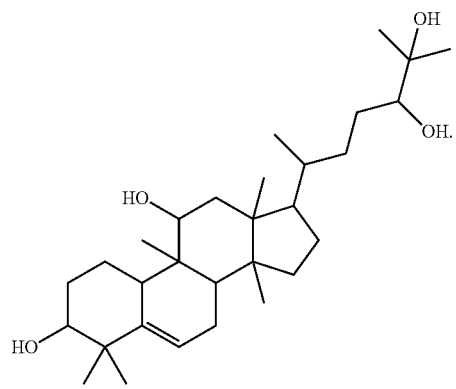

Formula IX

More preferably, the cucurbitane tetracyclic triterpenoid compound is mogroside IIIe (formula II), mogroside IVe (formula IV) or mogrol (formula IX).

In the application of the cucurbitane-tetracyclic triterpenoid compounds in preparation of drugs and/or health products for preventing and/or treating pulmonary fibrosis, a compound as shown in the formula I and a combination thereof as well as other human-acceptable pharmaceutical adjuvants are prepared into tablets, granules, decoctions or capsules.

The drugs and/or health products are capable of reducing accumulation volume of collagen in pulmonary fibrosis mesenchyme.

The drugs and/or health products are capable of relieving inflammation, inhibiting collagen formation and protecting lung tissue against pulmonary fibrosis.

The drugs and/or health products are capable of resisting pulmonary fibrosis by resisting inflammation and inhibiting alveolar epithelial-mesenchymal transition.

According to the disclosure, studies demonstrate that the mogroside compounds can improve bleomycin-induced mice pulmonary fibrosis. In-vivo experiments are performed to observe the pathological sections of lung tissue after Masson staining, determine the lung coefficients, body weight change and end body weights of each group, and detect the number of leukocytes and contents of TNF-α in the bronchoalveolar fluid of each group of mice at different stages, and the contents of HYP and TGF-β1 and the expression of α-SMA in lung tissue. The in-vitro experiments investigate that the mogroside compounds can significantly inhibit the NO release of LPS-induced mice macrophages RAW264.7 and TGF-β1-type II human lung type II epithelial-mesenchymal transition, and reduce the high expression of α-SMA after epithelial-mesenchymal transition after induction. The experimental results show that the mogroside compounds in the disclosure can improve the degrees pulmonary fibrosis of lung tissues in model mice, reduce collagen deposition in model lung tissue, improve epithelial-mesenchymal transition, and show a therapeutic effect on the mice pulmonary fibrosis model, and have a new medicine use for treating pulmonary fibrosis.

Embodiments of the disclosure will be further described in combination with examples below, but the disclosure is not limited to the scopes of these examples.

In the disclosure, mogroside IIIe (Example 1), mogroside IVe (Example 2) and mogrol (Example 3) are taken as examples to verify partial pharmacodynamic tests and results of mogroside compounds against pulmonary fibrosis.

In the disclosure, the preparation of mogroside IIIe, mogroside IVe and mogrol is as follows:

Mogroside V contained in total mogrosides extracted from natural grosvenor *Momordica* is the highest in content. After total mogrosides are hydrolyzed using 1-glucosidase, extracts containing different proportions of mogroside components can be obtained according to enzymolysis time. Mogrol is the aglycone of mogroside compounds, and can be obtained by acid hydrolysis.

Mogroside IIIe is obtained from commercially available *Momordica grosvenori* extracts via macroporous resin separation and high pressure reversed-phase preparative chromatography separation, and has a purity of 95% or more. Alternatively, by reference to a method for preparing mogroside IV in Chinese Patent 2010105610299, commercially available *Momordica grosvenori* extracts are hydrolyzed using 0-glucosidase, and then macroporous resin separation and high pressure reversed-phase preparative chromatography separation are carried out to obtain mogroside IIIe with a purity of 95% or more.

Mogroside IVe is obtained from commercially available *Momordica grosvenori* extracts via macroporous resin separation and high pressure reversed-phase preparative chromatography separation, and has a purity of 95% or more. Alternatively, by reference to a method for preparing mogroside IV in Chinese Patent 2010105610299, commercially available *Momordica grosvenori* extracts are hydrolyzed using 0-glucosidase, and then macroporous resin separation and high pressure reversed-phase preparative chromatography separation are carried out to obtain mogroside IV with a purity of 95% or more.

Mogrol is obtained by hydrolyzing commercially available *Momordica grosvenori* extracts with 5% sulfuric acid and purifying with silica gel, and has a purity of 95% or more.

Example 1 Improvement of Mogroside IIIe on Bleomycin-Induced Mice Pulmonary Fibrosis The above mogroside IIIe is selected to be subjected to in-vivo pharmacodynamical research. Injection of a bleomycin-induced mice pulmonary fibrosis model is a commonly used method in the world, and such model is similar to a human pulmonary interstitial fibrosis model.

1.1 Experimental Method 100 male ICR mice with a body weight of 25-30 g are provided by Comparative Medicine Center of Yangzhou University.

20 mice are used as a blank control group (control group in FIG. 1), and the other 80 mice are used for modeling. All the above mice are anesthetized by virtue of intraperitoneal injection of 4% chloral hydrate, with injection volume of 10 ml/kg. After anesthesia, each mouse is fixed and the neck of the mouse is disinfected; the skin of its neck is cut longitudinally with scissors to expose the trachea; the syringe is inserted into the trachea. The mice in the blank control group are injected with normal saline, and the remaining mice are injected with bleomycin (5 mg/kg); then the mouse plate is quickly erected and rotated, and the wound of each mouse is sutured after observing the breathing condition of the mouse, and 1-2 drops of penicillin injection are dropped at the suture. The postoperative mouse is placed back in a dry and clean mouse cage for rest, and then is normally fed after it revives approximately 1-2 h later.

Starting from the day 7 after modeling, the other 80 mice are randomly divided into a model group, a positive drug (prednisone acetate) group, a high-dose mogroside IIIe (50 mg/kg, mogroside IIIe-H) group, a low-dose mogroside IIIe group (10 mg/kg, mogroside IIIe-L), 20 mice in each group.

The mice in the blank control group and the model group are subjected to stomach perfusion with normal saline every day, the mice in the positive drug group are subjected to stomach perfusion with 6.67 mg/kg/d prednisone acetate, the mice in the high-dose/low-dose mogroside IIIe groups are subjected to stomach perfusion with 50 mg/kg/d and 10 mg/kg/d respectively for continuous 28 days, and are killed on the day 14 and the day 28. The each mouse is recorded in body weight, the lung tissue is taken out via dissection, cleaned with ice normal saline, sucked dry with absorbent paper and weighed, and then a lung coefficient is calculated, i.e., lung coefficient=lung weight (mg)/body weight (g). The left lung is put into 4% neutral formaldehyde for fixation, gradually dehydrated with alcohol, transparentized with xylene, immersed in wax, embedded in paraffin, then routinely sectioned and subjected to Masson staining, so that the lung tissue morphology, lung injury condition and pulmonary fibrosis degree are observed. Other lung lobes are individually stored for determination of HYP content.

All data are expressed as mean±SD(x±s). SPSS 11.5 statistical software is used for processing. Statistical analysis is performed using one-way ANOVA. $P<0.05$ represents this group has statistical significance.

1.2 Experimental Results 1.2.1 Influence of Mogroside IIIe on Body Weights of Model Mice Compared with the blank control group, the body weights of the mice in the model group are decreased significantly and all have statistical significance ($P<0.01$ or $0.05$). Compared with the body weight in the model group mice, the body weights of mice in the high-dose mogroside IIIe group, low-dose mogroside IIIe group and positive drug (prednisone acetate) group are obviously increased with statistical significance ($P<0.01$) after 14 and 28 days of administration. It indicates that mogroside IIIe can improve the physique of bleomycin-induced pulmonary fibrosis mice to different degrees at the doses of 20 mg/kg and 10 mg/kg and slow down the weight loss rate of the pulmonary fibrosis model mice, and the results are as shown in FIG. 1.

1.2.2 Influence of Mogroside IIIe on the Number of Leukocytes in the Bronchoalveolar Fluid of the Model Mice For mice lung tissue injury caused by bleomycin, the number of leukocytes is increased, especially neutrophil infiltration causes alveolar inflammation, and inflammatory cells release inflammatory mediators NO, TNF-α and various cytokines, thereby on one hand, aggravating lung tissue injury and on the other hand promoting excessive increase of collagen through various growth factors. This experiment is performed in accordance with requirement specification of a kit. The number of leukocytes in the bronchoalveolar lavage fluid of the mice in each group is detected by a colorimetric method on the day 14 (as shown in Table 1). Neutrophils and lymphocytes are obviously accumulated in the bronchoalveolar lavage fluid of the mice on the day 14 after treatment with bleomycin (BLM). Compared with the blank control group, the total number of cells and the number of neutrophils in the bronchoalveolar lavage fluid of the model group are both obviously increased (compared with the blank control group, ##$P<0.01$). After treatment with mogroside IIIe, the total number of cells and the number of neutrophils in the bronchoalveolar lavage fluid are obviously reduced than those in the individually administrated model group (compared with the model group, *P<0.05). It indicates that mogroside IIIe is capable of reducing the effusion of BLM-induced inflammatory cells.

TABLE 1

The total number of cells and the number of neutrophils in bleomycin-induced mice bronchoalveolar lavage fluid

| Group | Total number of cells | Number of neutrophils |
|---|---|---|
| Blank control group | 11.21 ± 3.98 | 1.02 ± 0.21 |
| Model group | 56.98 ± 23.76## | 18.32 ± 9.02## |
| Mogroside IIIe-H group (50 mg/kg) | 32.81 ± 18.53* | 4.28 ± 4.52* |

1.2.3 Influence of Mogroside IIIe on Lung Coefficients of Model Mice

Figure 2:
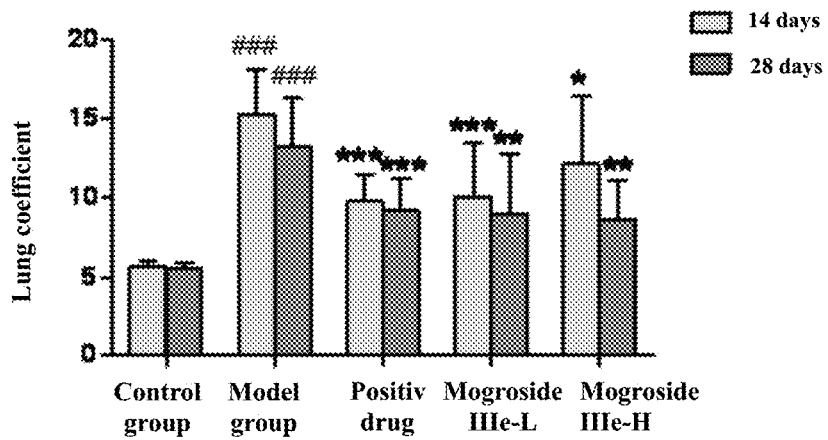
FIG. 2 is a schematic diagram showing influence of mogroside IIIe on change of lung coefficients of bleomycin-induced pulmonary fibrosis model mice; compared with the control group, ##$p<0.001$; compared with the model group, *$p<0.05$, **$p<0.01$; positive control drug: prednisone acetate.

Compared with the blank control group, the lung coefficients of mice in the model group are significantly increased and have statistical significance ($P<0.01$ or $0.05$); compared with the lung coefficients of mice in the model group, after administration for 14 days and 28 days, the lung coefficients of the mogroside IIIe drug group and the prednisone acetate group are both obviously decreased and have statistical significance ($P<0.01$). Compared with the blank control group, the lung coefficients of mice in the model group are obviously increased and have statistical significance ($P<0.01$ or $0.05$); compared with the body weights of mice in the model group, after administration for 14 days and 21 days, the lung coefficients of high-dose and low-dose mogroside IIIe groups and positive drug (prednisone acetate) group are all obviously decreased and have statistical significance ($P<0.01$). It indicates that mogroside IIIe can improve bleomycin-induced mice pulmonary fibrosis to different degrees and relieve the development degree of mice pulmonary fibrosis at the doses of 20 mg/k and 10 mg/kg (see FIG. 2).

1.2.4 Influence of Mogroside IIIe on Lung Tissues of Model Mice

Figure 3:
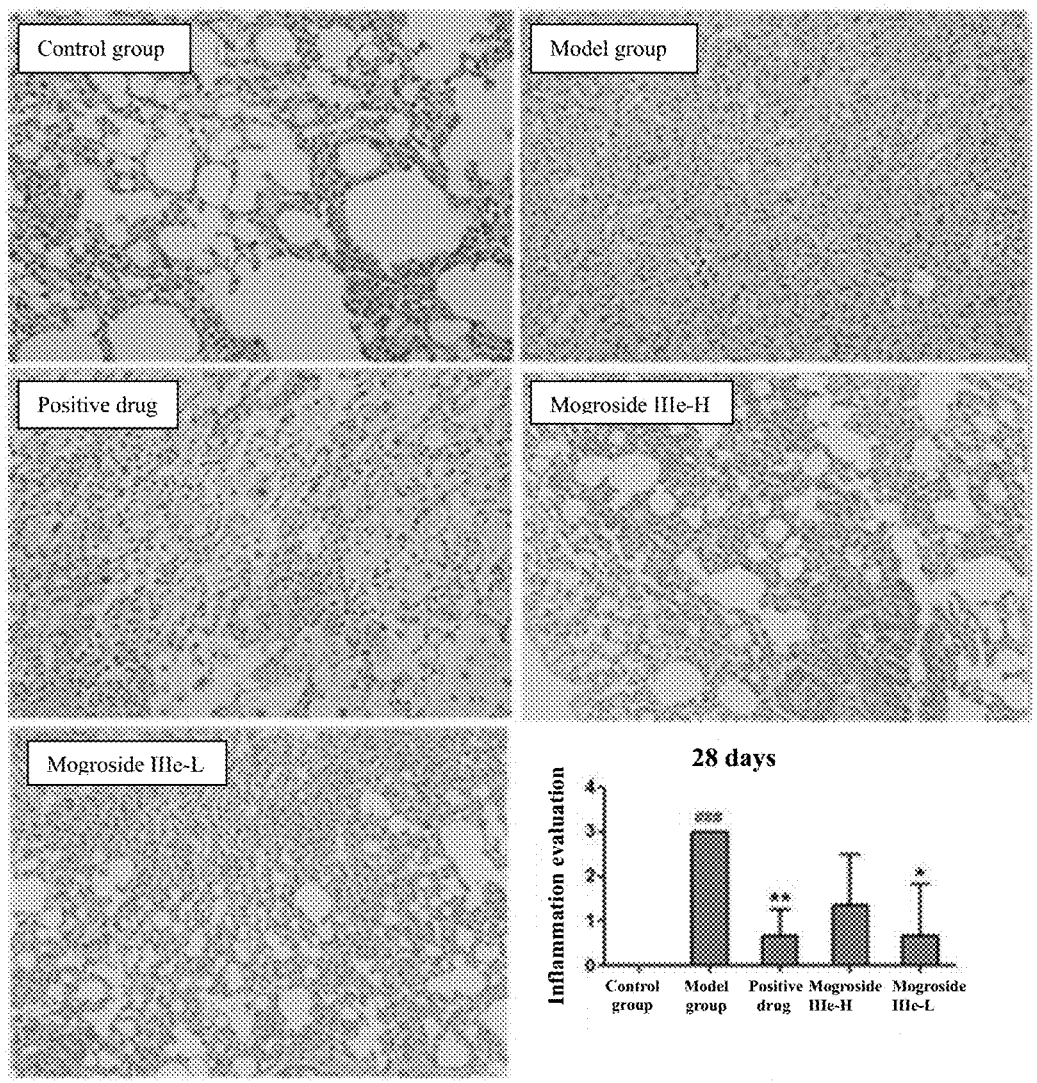
FIG. 3 is a schematic diagram showing influence of mogroside IIIe on lung tissue fibrosis degrees of each group of bleomycin-induced pulmonary fibrosis model mice (Masson staining); compared with the control group, ##$p<0.01$; compared with the model group, *$p<0.05$, **$p<0.01$; positive control drug: prednisone acetate.

A pathological tissue section of lung on the day 28 is subjected to Masson staining, and a result indicates that lung tissue structures of mice in the blank control group are complete and clear, pulmonary alveoli septum is not thickened, an alveolar space is transparent and does not contain obvious effusion, and no fibroblasts are proliferated; a few of collagenous fibers stained into blue can be seen in the lung tissues of mice in the blank control group, which are main components of an extracellular matrix. The alveoli structures of mice in the model group are damaged, pulmonary alveoli septum is widened, a large amount of inflammatory cells are infiltrated into acute fibrocyte hyperplasia, a large amount of collagens are deposited, pulmonary fibrosis is formed, a large amount of dense collagenous fibers dyed into blue, which are deposited in a sarciniform or a sheet form, can be seen after Masson staining, and all of them basically meet features of pulmonary fibrosis, thereby indicating that an experiment mice pulmonary fibrosis model is successfully prepared. After treatment with mogroside IIIe, it can be seen that the lung tissue structures of mice are complete and clear, pulmonary alveoli septum is slightly thickened, and fibroblast hyperplasia degree is lower than that in the model group. After treatment with positive drug prednisone acetate, pulmonary alveoli septum of mice in the positive group is wider, the alveolar space is narrowed, multiple fibroblasts are proliferated, and the degree of the lesion is relieved than that in the model group. Compared with the model group, the fibrosis degrees of various administration groups and positive drug groups are all relieved (see FIG. 3).

Figure 4:
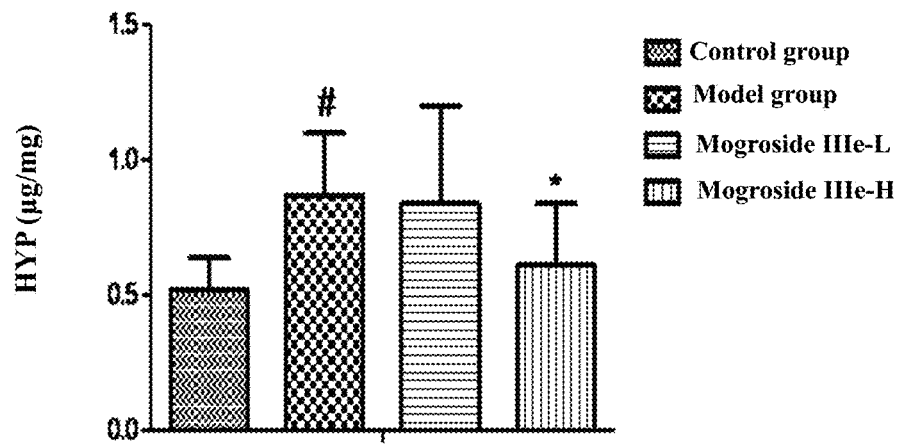
FIG. 4 is a schematic diagram showing influence of mogroside IIIe on contents of HYP in lung tissues of bleomycin-induced pulmonary fibrosis model mice; compared with the control group, #$p<0.05$; compared with the model group, *$p<0.05$.

1.2.5 Influence of Mogroside IIIe on HYP Contents of Lung Tissues of Model Mice Lung Tissue Hydrooxyproline (HPY) is an amino acid obtained through protein hydrolysis of connective tissues, accounts for about 14% of the weight of collagen and plays a crucial role in stability of collagen. Since the collagen is an only protein having high HYP content, determination of HYP content can reflect total amount change of tissue collagen. The content of HYP in the lung tissue is detected adopting a digestion method. Compared with the blank control group, the HYP content of the lung tissue in the model group is obviously increased ($P<0.01$) at the day 28; compared with the model group, the drug can obviously reduce the content of HYP in the lung tissue ($P<0.05$). It indicates that mogroside IIIe can improve bleomycin-induced mice pulmonary fibrosis to different degrees at the dose of 50 mg/kg, mogroside IIIe can reduce the content of collagenous fibers of the model tissue and slow down the development degree of pulmonary fibrosis of mice in the model mice (as shown in FIG. 4).

1.2.6 Influence of Mogroside IIIe on α-SMA Level of TGF-β1-Induced Human Pulmonary Alveoli Type II Epithelial Cells Alveolar epithelial cells can obtain mesenchymal cell phenotypes through an epithelial cell-mesenchyme transformation (EMT) process to serve as an important source of myofibroblast and muscle fiber metrocyte. In this new mode, epithelial cell-mesenchyme transformation of pulmonary alveoli should be considered as one of key links of fibrosis. In mature cells, injury can induce transformation of epithelial cells into mesenchymal cell phenotype, thus facilitating the fibrosis of many organs. Fibroblasts and muscle fiber metrocytes differentiated from epithelial cells often change through form (for example, change from a cubical cell form to a strip form or a fusiform), obtaining of specific marker of the fibroblast or the muscle fiber metrocyte (for example, α-SMA) and loss of the epithelial character marker (for example, epithelial cell cadherin (E-cadherin and closely linked protein) are fussed together with these epithelial tissues. Through an in-vitro test, A549 cells are induced with TGF-β1 to generate epithelial cell-mesenchyme transformation (EMT), the α-SMA expression level of actin is analyzed adopting a Western blot method, and study meaning of mogroside IIIe on pathogensis of pulmonary fibrosis in a signal transduction pathway of an EMT process is discussed.

Figure 5:
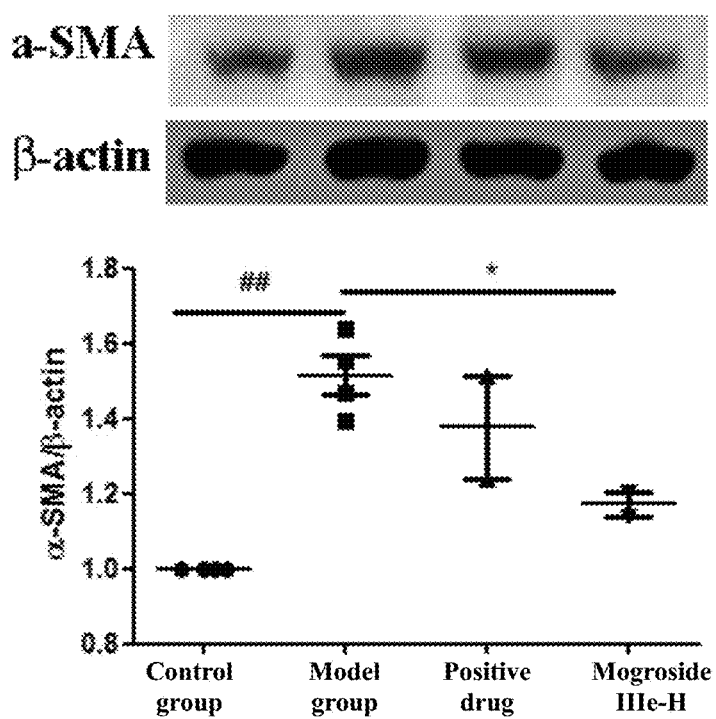
FIG. 5 is a schematic diagram showing influence of mogroside IIIe on α-SMA expression level in TGF-β1-induced human alveoli type II epithelial cells. compared with the control group, ##$p<0.01$; compared with the model group, *$p<0.05$.

In the disclosure, well grown A549 cells subcultured by 2-4 generations perform $1\times10^5$ passage and then are divided into four groups, and serum-free DMEM culture solution is added to perform starvation for 12 hours, so that cells are in the same growth level. For the model group, TGF-β1 having a concentration of 5 ng/mL is added in a serum-free culture medium; for the positive drug group and mogroside IIIe group (100 μM), TGF-β1 having a concentration of 5 ng/mL and corresponding drugs are added. After culture for 48 hours, change of lung epithelial cells is observed under an inverted microscope, influence of TGF-β1 on an expression level of a marker protein α-SMA for transforming A549 epithelial cells into mesenchymal cells is detected with Western blot. An experiment result indicates that compared with the blank control group, the expression of mesenchymal cell marker α-SMA is up-regulated after TGF-β1 is added in A549 cells, and mogroside IIIe can significantly inhibit α-SMA caused by TGF-β1 under the concentration of 50 μM (see FIG. 5).

1.2.7 Discussion:

Compared with the model group, high-dose/low-dose mogroside IIIe groups can obviously reduce the index of lung, the content of HYP in the lung tissue from the high-dose group is obviously reduced (p<0.05), and a pathological result shows that the lung tissue structure of the mogroside IIIe drug group is obviously improved, the pulmonary alveoli structure is damaged and the thickening degree of alveolar septum is obviously alleviated, inflammatory cell infiltration is reduced, and collagenous fiber content is reduced. Compared with the blank control group, the number of neutrophils in bronchoalveolar lavage fluid of mice in the model group is significantly increased, indicating that bleomycin causes inflammatory reaction in the model group so as to initiate in-vivo inflammatory cascade reaction. However, after the drug is administrated, inflammation and fibrosis degrees of mice are reduced to different degrees, and the content of HYP in the lung tissue is significantly reduced, indicating that the drug can protect lung cells from being injured so as to prevent and treat pulmonary fibrosis. An in-vitro experiment result shows that mogroside IIIe can inhibit TGF-β1-induced epithelial-mesenchymal transition at a concentration of 50 μM and reduce lung fibroblast marker α-SMA.

In summary, in-vivo and in-vitro experiment results show that mogroside IIIe can improve inflammation and fibrosis degrees of lung tissues in the bleomycin mice pulmonary fibrosis model and generation of collagen in the lung tissue, and effectively inhibits human pulmonary alveoli type II epithelial-mesenchymal transition caused by the cell growth factor TGF-β1, and mogroside IIIe has a new use for treating pulmonary fibrosis.

Example 2 Improvement of Mogroside IVe on Mice Pulmonary Fibrosis Caused by Bleomycin Induction The above mogroside IVe (formula IV) is selected to carry out in-vivo pharmacodynamic study.

2.1 Experiment Method 100 male ICR mice with a body weight of 25-30 g are provided by Comparative Medicine Center of Yangzhou University.

20 mice are used as a blank control group, and the other 80 mice are used for modeling. All the above mice are anesthetized by virtue of intraperitoneal injection of 4% chloral hydrate, with injection volume of 10 ml/kg. After anesthesia, each mouse is fixed and the neck of the mouse is disinfected. The skin of its neck is cut longitudinally with scissors, and fascia and muscles are longitudinally and bluntly tore with tweezers to expose the trachea. The syringe is inserted into the trachea. The mice in the blank control group are injected with normal saline, and the remaining mice are injected with bleomycin (5 mg/kg); then the mouse plate is quickly erected and rotated, the breathing condition of the mouse is observed, the wound of the neck is disinfected with 75% alcohol cotton after being rotated and then sutured, and 1-2 drops of penicillin injection are dropped at the suture. The postoperative mouse is placed back in a dry and clean mouse cage for rest, and then is normally fed after it revives approximately 1-2 h later.

Starting from the day 7 after modeling, the other 80 mice are divided into a model group, a positive drug (prednisone acetate) group, a high-dose mogroside IVe group (50 mg/kg, mogroside IVe-H) and a low-dose mogroside IVe group (50 mg/kg, mogroside IVe-L), 20 mice in each group.

The mice in the blank control group and the model group are subjected to stomach perfusion with normal saline every day, the mice in the positive drug group are subjected to stomach perfusion with 6.67 mg/kg/d prednisone acetate, the mice in the high-dose/low-dose mogroside IVe groups are subjected to stomach perfusion with 50 mg/kg/d (high-dose group) and 20 mg/kg/d (low-dose group) respectively for continuous 28 days, and the body weights are weighed and recorded; and the mice are killed on the day 28. The lung tissue is taken out via dissection, and a lung coefficient is calculated, i.e., lung coefficient=lung weight (mg)/body weight (g). The left lung is put into 4% neutral formaldehyde for fixation, gradually dehydrated with alcohol, transparentized with xylene, immersed in wax, embedded in paraffin, then routinely sectioned and subjected to Masson staining, so that the lung tissue morphology, lung injury condition and pulmonary fibrosis degree are observed.

All data are expressed as mean±SD(x̄±s). SPSS11.5 statistical software is used for processing, statistical analysis is performed using one-way ANOVA, P<0.05 represents this group has statistical significance.

Figure 6:
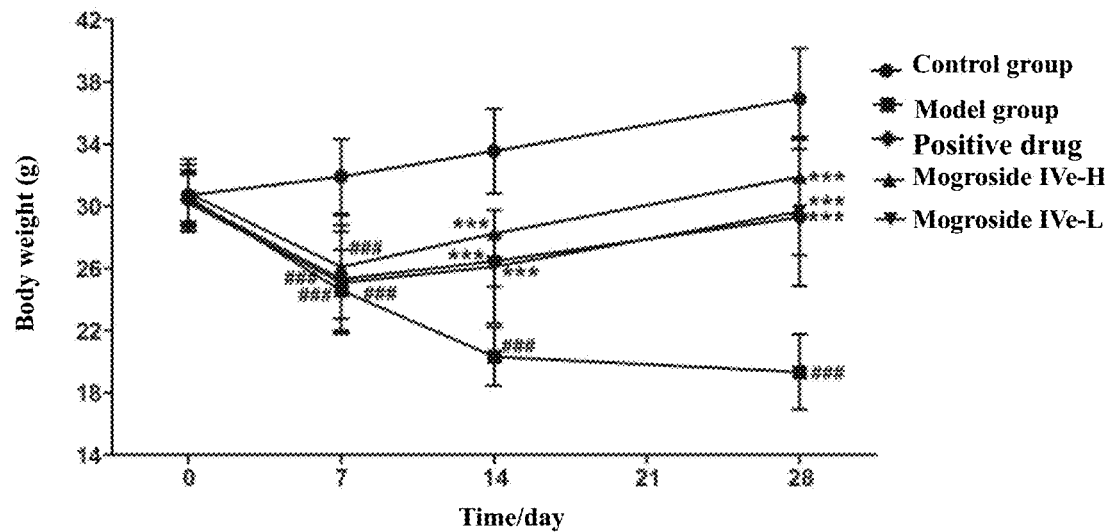
FIG. 6 is a schematic diagram showing change trends of mogroside IVe on changes of body weights of bleomycin-induced pulmonary fibrosis model mice; compared with the control group, #$p<0.05$; compared with the model group, *$p<0.05$, **$p<0.01$; positive control drug: prednisone acetate.

2.2 Experiment Result 2.2.1 Influence of Mogroside IVe on Body Weights of Pulmonary Fibrosis Model Mice Compared with the blank control group, the body weights of mice in the model group are obviously decreased and have statistical significance (P<0.01 or 0.05); compared with the body weights of mice in the model group, the body weights of the high-dose/low-dose mogroside IVe groups and positive drug (prednisone acetate) groups are all obviously increased after administration for 14 days and 28 days and have statistical significance (P<0.01). It indicates that mogroside IVe can improve the physique of bleomycin-induced mice pulmonary fibrosis to different degrees at the doses of 50 mg/kg and 20 mg/kg and relieve the reduction degrees of the body weights of the lung model mice (see FIG. 6).

2.2.2 Influence of Mogroside IVe on the Number of Leukocytes in Bronchoalveolar Lavage Fluid of the Model Mice For tissue injury caused by bleomycin, the number of leukocytes is increased, especially, neutrephil infiltration causes pulmonary alveoli inflammation, and inflammatory cells release inflammatory mediators NO, TNF-α and various cytokines, thereby on one hand, aggravating lung tissue injury and on the other hand promoting excessive increase of collagen through various growth factors. This experiment is performed in accordance with requirement specification of a kit. The number of leukocytes in the bronchoalveolar lavage fluid of the mice in each group is detected by a colorimetric method on the day 14 (as shown in Table 2). Neutrophils and lymphocytes are obviously accumulated in the bronchoalveolar lavage fluid of the mice on the day 14 after treatment with bleomycin (BLM). Compared with the blank control group, the total number of cells and the number of neutrophils in the bronchoalveolar lavage fluid of the model group are both obviously increased (compared with the blank control group, ##P<0.01). After treatment, the total number of cells and the number of neutrophils in the bronchoalveolar lavage fluid are obviously reduced than those in the individually administrated model group (compared with the model group, *P<0.05). It indicates that mogroside IVe is capable of reducing the effusion of BLM-induced inflammatory cells.

TABLE 2

Influence on the total number of cells and the number of the neutrophils in bronchoalveolar lavage fluid of mice after bleomycin induction ($\times 10^4$, n = 5)

| Group | Total No. of cells | No. of neutrophils |
| --- | --- | --- |
| Blank control group | 12.26 ± 3.74 | 1.36 ± 0.23 |
| Model group | 58.93 ± 21.47## | 19.26 ± 9.65## |
| Mogroside IVe high-dose group (50 mg/kg) | 30.84 ± 16.49* | 3.97 ± 3.89* |

2.2.3 Influence of Mogroside IVe on Lung Coefficients of Model Mice

Figure 7:
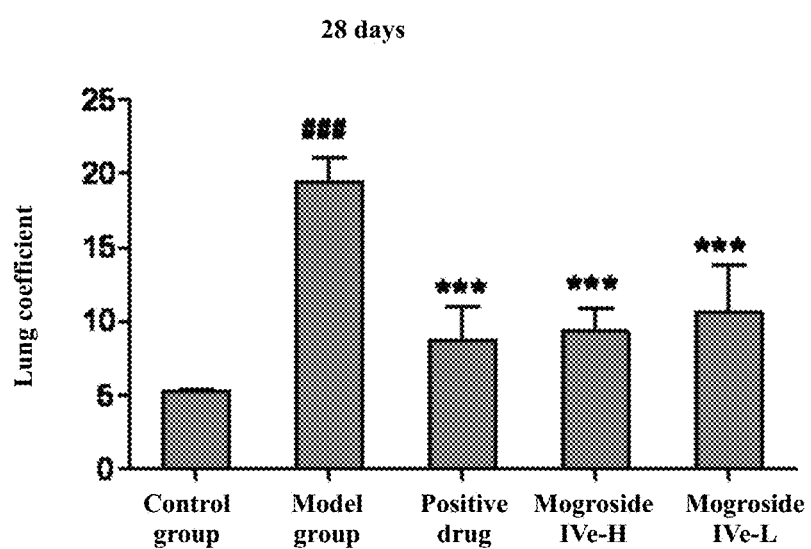
FIG. 7 is a schematic diagram showing influence of mogroside IVe on change of lung coefficients of bleomycin-induced pulmonary fibrosis model mice; compared with the control group, ##$p<0.001$; compared with the model group, *$p<0.05$, **$p<0.01$; positive control drug: prednisone acetate.

The lung coefficient is measured on the day 28 after modeling. Compared with the blank control group, the lung coefficients of mice in the model group are obviously increased and have statistical significance (P<0.01 or 0.05); compared with the lung coefficients of mice in the model group, the lung coefficients of the mogroside IVe drug group and the prednisone acetate group are all obviously reduced and have statistical significance (P<0.01). Compared with the blank control group, the lung coefficients of mice in the model group are obviously increased and have statistical significance (P<0.01 or 0.05); compared with the body weights of mice in the model group, the lung coefficients of the high-dose/low-dose mogroside IVe groups and the positive drug (prednisone acetate) group are all obviously reduced and have statistical significance (P<0.01). It indicates that mogroside IVe can improve bleomycin-induced mice pulmonary fibrosis to different degrees at the doses of 50 mg/kg and 20 mg/kg and relieve the development degree of the mice pulmonary fibrosis (see FIG. 7).

2.2.4 Influence of Mogroside IVe on Lung Tissues of the Model Mice

Figure 8:
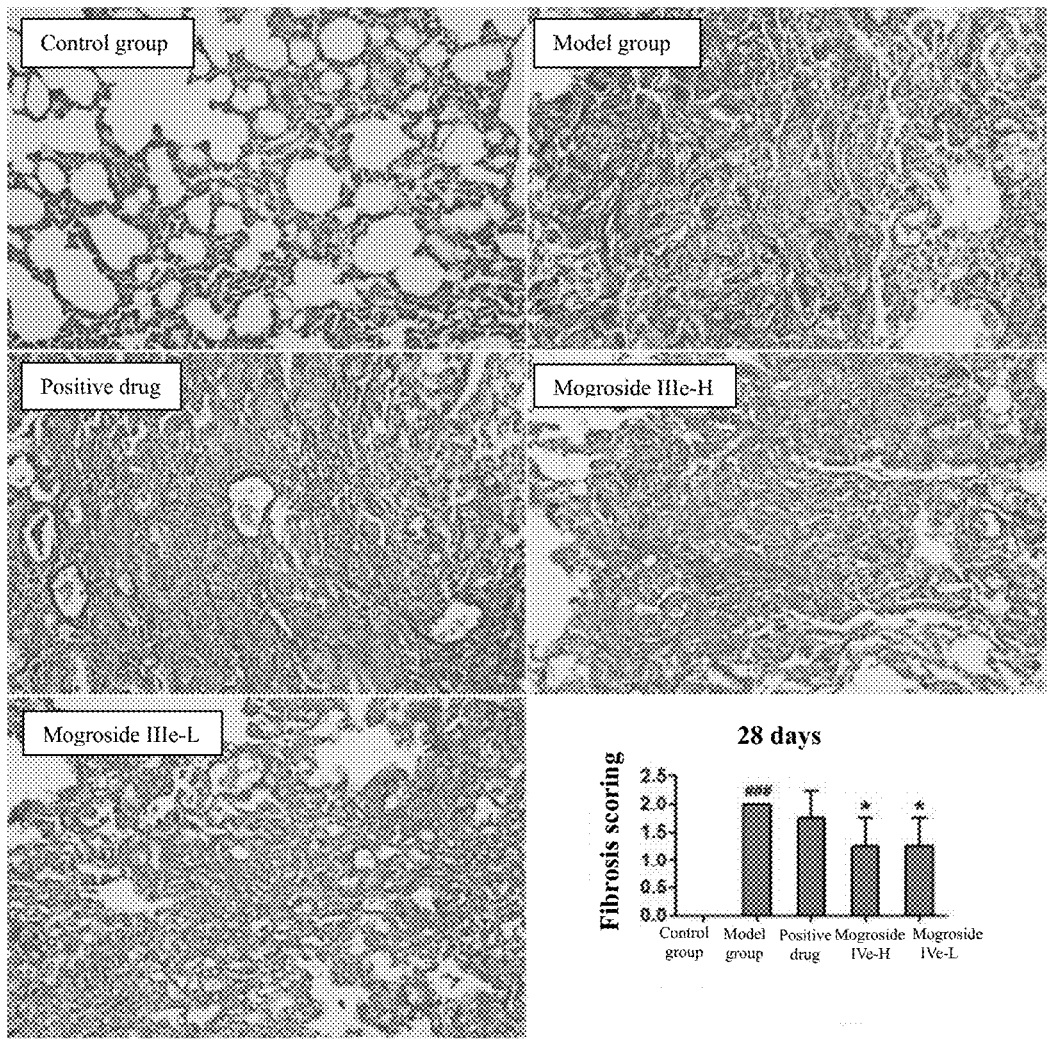
FIG. 8 is a schematic diagram showing influence of mogroside IVe on pulmonary fibrosis degrees of each group of bleomycin-induced pulmonary fibrosis model mice (Masson staining); compared with the control group, ##$p<0.01$; compared with the model group, *$p<0.05$, **$p<0.01$; positive control drug: prednisone acetate.

A pathological tissue section is subjected to Masson staining, and a result indicates that lung tissue structures of mice in the blank control group are complete and clear, pulmonary alveoli septum is not thickened, an alveolar space is transparent, and no fibroblasts are proliferated; a few of collagenous fibers stained into blue can be seen in the lung tissues of mice in the blank control group, which are main components of an extracellular matrix. The alveoli structures of mice in the model group are damaged, pulmonary alveoli septum is widened, a large amount of collagens are deposited, pulmonary fibrosis is formed, a large amount of dense collagenous fibers stained into blue, which are deposited in a sarciniform or a sheet form, can be seen after Masson staining, and all of them basically meet features of pulmonary fibrosis, thereby indicating that an experiment mice pulmonary fibrosis model is successfully prepared. After treatment with mogroside IVe, it can be seen that the lung tissue structures of mice are complete and clear, pulmonary alveoli septum is slightly thickened, and fibroblast hyperplasia degree is lower than that in the model group. Compared with the model group, the fibrosis degrees of various administration groups and positive drug groups are all relieved (see FIG. 8).

2.2.5 Discussion:

Compared with the model group, high-dose/low-dose mogroside IVe groups can obviously reduce lung index, pathological results show that lung tissue structures of the high-dose/low-dose mogroside IVe groups and mogrol drug groups are obviously improved. Compared with the blank control group, the number of neutrophils in the bronchoalveolar lavage fluid of mice in the model group is significantly increased, indicating that in the model group, bleomycin causes inflammatory reaction, thereby initiating in-vivo inflammatory cascade reaction. After the drug is administrated, inflammation and fibrosis degrees of mice are relieved to different degrees, indicating that the drug can protect lung cells from being damaged so as to prevent and treat pulmonary fibrosis. An in-vivo experiment result indicates that mogroside IVe can improve lung tissue inflammation and pulmonary fibrosis degree in a bleomycin mice pulmonary fibrosis model and generation of collagens in lung tissue, and mogroside IVe has a new use of treating pulmonary fibrosis.

Example 3 Improvement of Mogrol on Bleomycin-Induced Mice Pulmonary Fibrosis Mogrol (formula IX) is selected to carry out the following in-vivo pharmacodynamic study.

3.1 Experiment Method 100 male ICR mice with a body weight of 25-30 g are provided by Comparative Medicine Center of Yangzhou University.

20 mice are used as a blank control group, and the other 80 mice are used for modeling. All the above mice are anesthetized by virtue of intraperitoneal injection of 4% chloral hydrate, with injection volume of 10 ml/kg. After anesthesia, each mouse is fixed and the neck of the mouse is disinfected; the skin of its neck is cut longitudinally with scissors, and fascia and muscles are longitudinally and bluntly tore with tweezers to expose the trachea; the syringe is inserted into the trachea. The mice in the blank control group are injected with normal saline, and the other mice are injected with bleomycin (5 mg/kg); then the mouse plate is quickly erected and rotated, the breathing condition of the mouse is observed, the wound of the neck is disinfected with 75% alcohol cotton after being rotated and then sutured, and 1-2 drops of penicillin injection are dropped at the suture. The postoperative mouse is placed back in a dry and clean mouse cage for rest, and then is normally fed after it revives approximately 1-2 h later. Starting from the day 7 after modeling, the other mice are randomly divided into a model group, a positive drug (prednisone acetate) group, a high-dose mogrol group (50 mg/kg, mogrol-H) and a low-dose mogrol group (20 mg/kg, mogrol-L), 20 mice in each group.

The mice in the blank control group and the model group are subjected to stomach perfusion with normal saline every day, the mice in the positive drug group are subjected to stomach perfusion with 7.0 mg/kg/d prednisone acetate, the mice in the high-dose/low-dose mogrol groups are subjected to stomach perfusion for continuous 28 days, and the body weights are weighed and recorded; and the mice are killed on the day 28. The lung tissue is taken out via dissection, fixed in 4% neutral formaldehyde, gradually dehydrated with alcohol, transparentized with xylene, immersed in wax, embedded in paraffin, then routinely sectioned and subjected to Masson staining, so that the lung tissue morphology, lung injury condition and pulmonary fibrosis degree are observed.

All data are expressed as mean±SD(x±s). SPSS11.5 statistical software is used for processing, statistic analysis is performed adopting one-way ANOVA, and P<0.05 represents this group has significant difference.

3.2 Experiment Result

Figure 9:
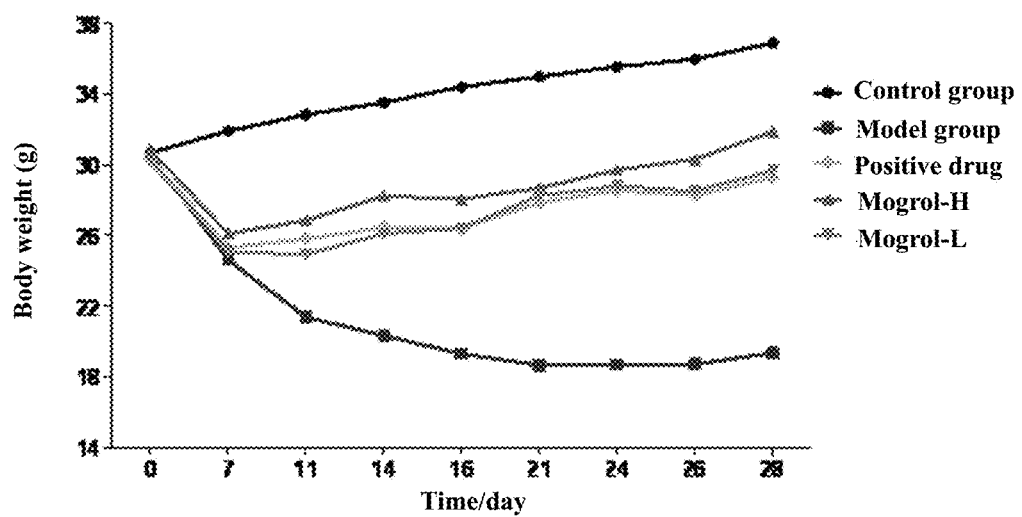
FIG. 9 is a schematic diagram showing change trend of mogrol on body weights of bleomycin-induced pulmonary fibrosis model mice; compared with the control group, #$p<0.05$; compared with the model group, *$p<0.05$, **$p<0.01$; positive control drug: prednisone acetate.

3.2.1 Influence of Mogrol on Body Weights of Pulmonary Fibrosis Model Mice Compared with the body weights of mice in the model group, the body weights of high-dose/low-dose mogrol groups and positive drug (prednisone acetate) group are all obviously increased. It indicates that mogrol can improve the physique of bleomycin-induced mice pulmonary fibrosis to different degrees at the doses of 50 mg/kg and 20 mg/kg and relive the reduction degrees of the body weights of the model mice (see FIG. 9).

3.2.2 Influence of Mogrol on the Number of Leukocytes in the Bronchoalveolar Lavage Fluid of Model Mice For mice lung tissue injury caused by bleomycin, the number of leucocytes is increased, especially neutrophil infiltration causes pulmonary alveoli inflammation, inflammatory cells release inflammatory mediators NO, TNF-α and various cytokines, thereby on one hand, aggravating lung tissue injury and on the other hand promoting excessive increase of collagen through various growth factors. This experiment is performed in accordance with requirement specification of a kit. The number of leukocytes in the bronchoalveolar lavage fluid of the mice in each group is detected by a colorimetric method on the day 14 (the results are as shown in Table 3). Compared with the blank control group, the total number of cells and the number of neutrophils in the bronchoalveolar lavage fluid of mice in the model group are both obviously increased (compared with the blank control group, ##P<0.01). After treatment with mogrol (50 mg/kg, the total number of cells and the number of neutrophils in the bronchoalveolar lavage fluid are obviously reduced than those in the individually administered model group (compared with the model group, *P<0.05). It indicates that mogrol is capable of reducing effusion of BLM-induced inflammatory cells.

TABLE 3

Influence on the total number of the cells and the number of the neutrophils in bleomycin-induced mice bronchoalveolar lavage fluid ($\times 10^4$, n = 5)

| Group | Total No. of cells | No. of neutrophils |
|---|---|---|
| Blank control group | 13.16 ± 3.74 | 1.96 ± 0.65 |
| Model group | 65.13 ± 21.57## | 18.26 ± 9.45## |
| high-dose mogrol group (50 mg/kg) | 34.72 ± 17.83** | 4.16 ± 4.26** |

3.2.3 Influence of Mogrol on Lung Tissues of Model Mice

Figure 10:
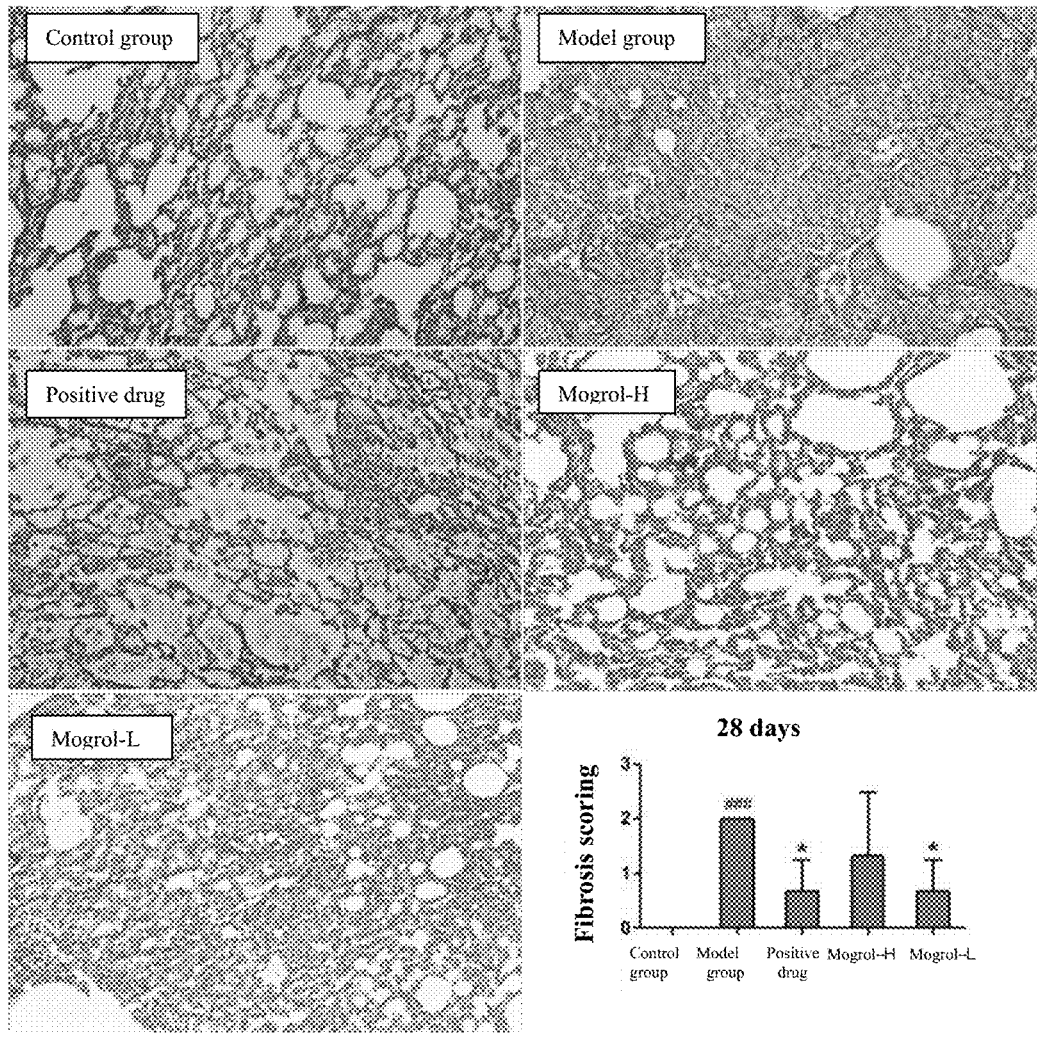
FIG. 10 is a schematic diagram showing influence of mogrol on pulmonary fibrosis degrees of each group of bleomycin-induced pulmonary fibrosis model mice (Masson staining); compared with the control group, ##$p<0.01$; compared with the model group, *$p<0.05$, **$p<0.01$; positive control drug: prednisone acetate.

A few of collagenous fibers stained into blue can be seen in the lung tissues of mice in the blank control group, which are main components of an extracellular matrix. The pulmonary alveoli structures of mice in the model group are damaged, pulmonary alveoli septum is widened, a large amount of collagens are deposited, pulmonary fibrosis is formed, a large amount of dense collagenous fibers stained into blue, which are deposited in a sarciniform or a sheet form, are seen after Masson staining, and all of them basically meet features of pulmonary fibrosis, indicating that an experiment mice pulmonary fibrosis model is successfully prepared. After treatment with high-dose/low-dose mogrol (50, 20 mg/kg), it can be seen that the lung tissue structures of mice are complete and clear, pulmonary alveoli septum is thickened, and fibroblast hyperplasia degree is lower than that in the model group. Compared with the model group, fibrosis degrees of various administration groups are all reduced (see FIG. 10).

3.2.5 Discussion:

Compared with the model group, high-dose/low-dose mogrol groups can obviously reduce lung index, and pathological results show that the lung tissue structure of the mogrol drug group is obviously improved. Compared with the blank control group, the number of neutrophils in the bronchoalveolar lavage fluid of mice in the model group is significantly increased, indicating that in the model group, bleomycin causes inflammatory reaction; and after the drug is administrated, inflammation and fibrosis degrees of mice are relieved to different degrees, indicating that the drug can protect lung cells from being injured so as to prevent and treat pulmonary fibrosis. As an aglucon of a cucurbitane tetracylic triterpenoid compound, mogrol has common nuclear parent in this compound structure skeleton. An in-vivo experiment result discloses that the in-vivo experiment result shows that mogrol can improve the pulmonary fibrosis degree of the lung tissue in a bleomycin mice pulmonary fibrosis model, indicating a new use of this component in preparation of a drug for preventing or treating pulmonary fibrosis.

We claim:

1. A method for treating pulmonary fibrosis induced by TGF-β1 (transforming growth factor-β1) in a patient in need thereof, comprising administering to the patient an effective amount of a cucurbitane tetracyclic triterpenoid compound, wherein the formula of the cucurbitane tetracyclic triterpenoid compound is as follows:

Formula II

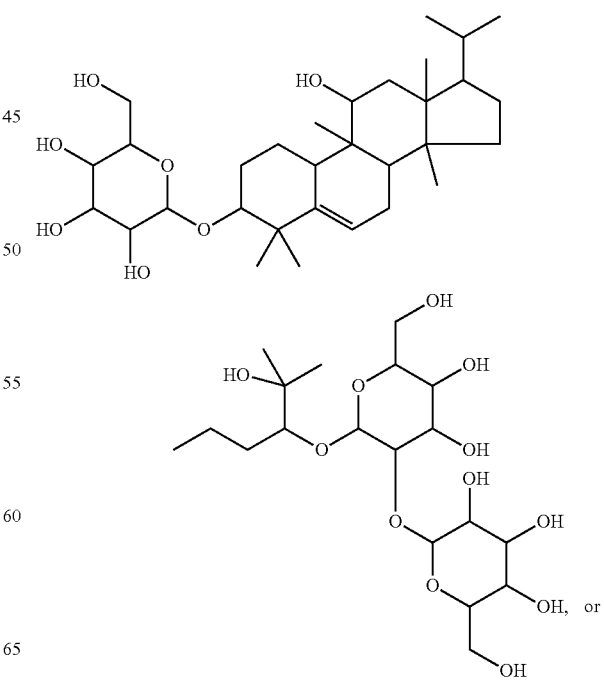

Formula III
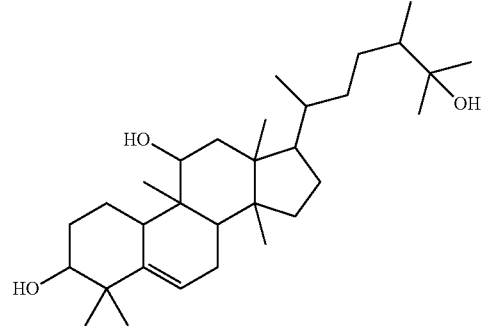
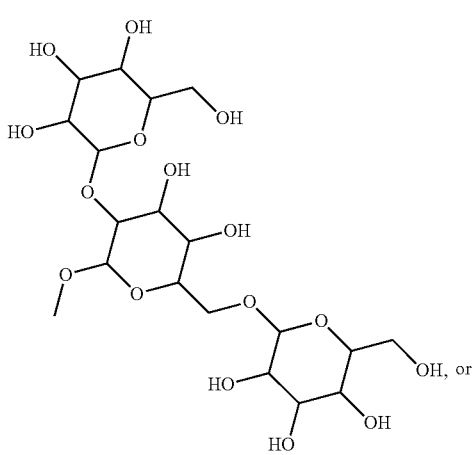
Formula IV
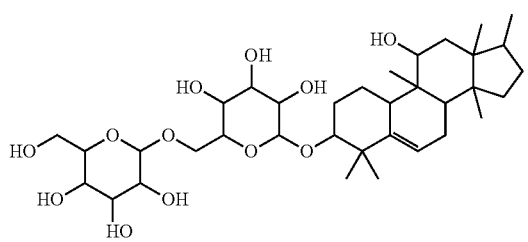
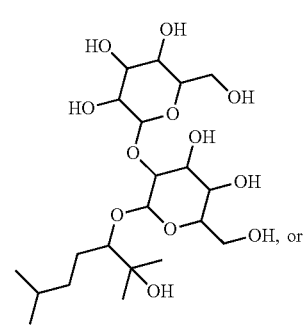
Formula VI
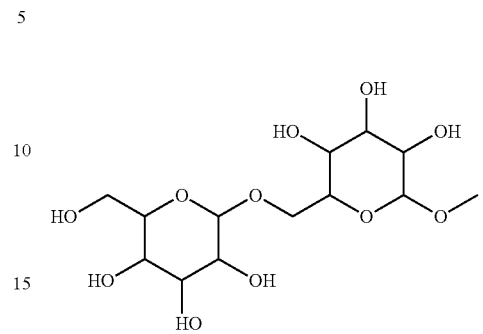
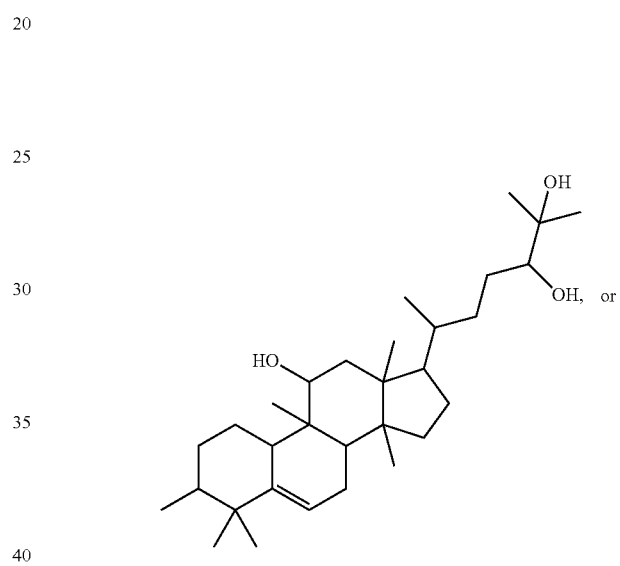
Formula VII
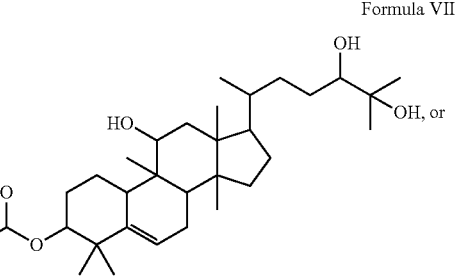

Formula VIII

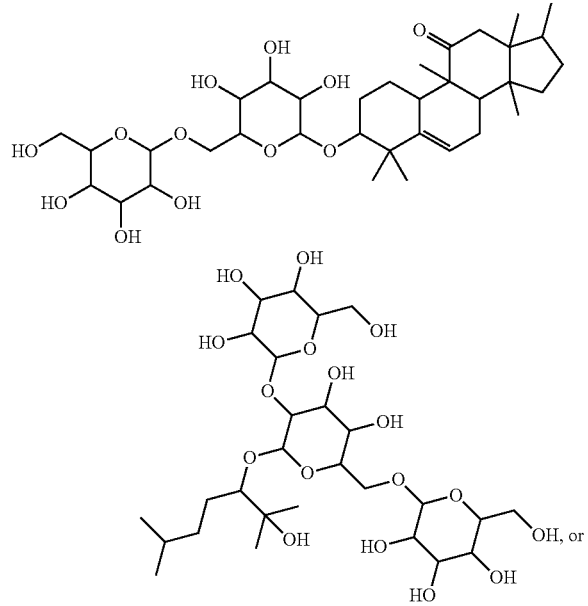

Formula IX

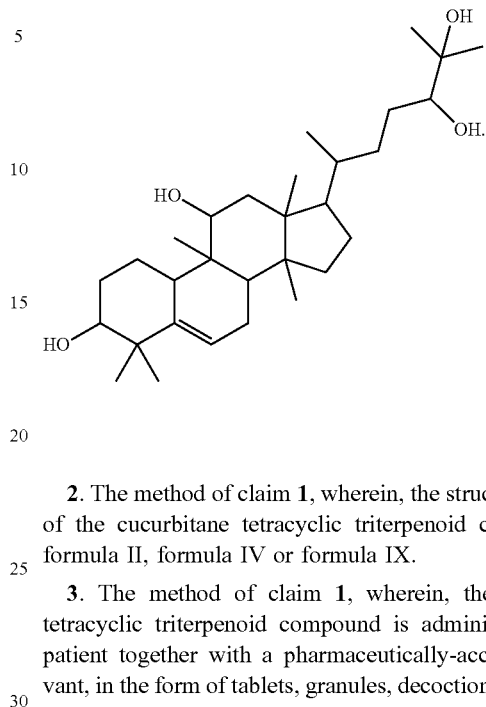

2. The method of claim 1, wherein, the structural formula of the cucurbitane tetracyclic triterpenoid compounds is formula II, formula IV or formula IX.

3. The method of claim 1, wherein, the cucurbitane tetracyclic triterpenoid compound is administered to the patient together with a pharmaceutically-acceptable adjuvant, in the form of tablets, granules, decoctions or capsules.

* * * * *